United States Patent
Lai

(10) Patent No.: US 8,475,719 B1
(45) Date of Patent: Jul. 2, 2013

(54) ELECTRIC CENSER

(75) Inventor: Chih-Chen Lai, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/570,225

(22) Filed: Aug. 8, 2012

(30) Foreign Application Priority Data

Mar. 16, 2012 (TW) .............................. 101108976 A

(51) Int. Cl.
*A61L 2/00* (2006.01)
(52) U.S. Cl.
USPC .......................................... 422/125; 422/120
(58) Field of Classification Search
USPC ...................... 422/125, 120, 5, 126
See application file for complete search history.

(56) References Cited

U.S. PATENT DOCUMENTS

2007/0031089 A1* 2/2007 Tessnow et al. ................ 385/49
2011/0199782 A1* 8/2011 Poisel et al. ................... 362/579

FOREIGN PATENT DOCUMENTS

JP 2002-262990 * 9/2002
WO WO 2011045211 * 4/2011

OTHER PUBLICATIONS

English machine translation of Moritomo JP-2002-262990. Sep. 17, 2002. Retrieved from Industrial Property Digital Library.*
PolymerProcessing.com "Poly(ethylene terephthalate) (PET)". Retrieved from Internet Archive Wayback Machine Capture from Apr. 29, 2010.*
Kwan. Principles of Optical Fibers. San Jose State University. Fall 2002.*

* cited by examiner

*Primary Examiner* — Sean E Conley
*Assistant Examiner* — Donald Spamer
(74) *Attorney, Agent, or Firm* — Altis Law Group, Inc.

(57) ABSTRACT

An electric censer includes a censer body, a receiving unit and an incense branch. The censer body is a hollow container with an opening defined at a top thereof. The receiving unit is received in the censer body and includes a hollow tube communicating with the opening of the censer body. The incense branch includes a light guiding bar and a light emitting unit positioned on a bottom end the light guiding bar. A top end of the light guiding bar extends outwardly from the opening of the censer body and act as a light outputting side of the incense branch. The position of the light emitting unit is adjustable by pressing or pulling the light guiding bar.

16 Claims, 3 Drawing Sheets

ELECTRIC CENSER

BACKGROUND

1. Technical Field

The present disclosure generally relates to a censer, and particularly to an electric censer.

2. Description of Related Art

Traditional censers are used for accommodating incenses, each of which mainly includes a rod made of bamboo and aromatic biotic materials coated on the rod. When the aromatic biotic materials are burned, large amounts of smoke are released. The burning incenses could ignite other articles to burn which may cause fire accident; furthermore, the released smoke not only pollutes the environment, but also is harmful to health.

Therefore, traditional censers are replaced by electric censers. The electric censers each includes a censer body and an incense branch fixed on the censer body. However, the incense branch is made of quartz glass which is easy to crack.

Therefore, what is needed is to provide an electric censer capable of overcoming the above shortcomings.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure.

DETAILED DESCRIPTION

Figure 1:
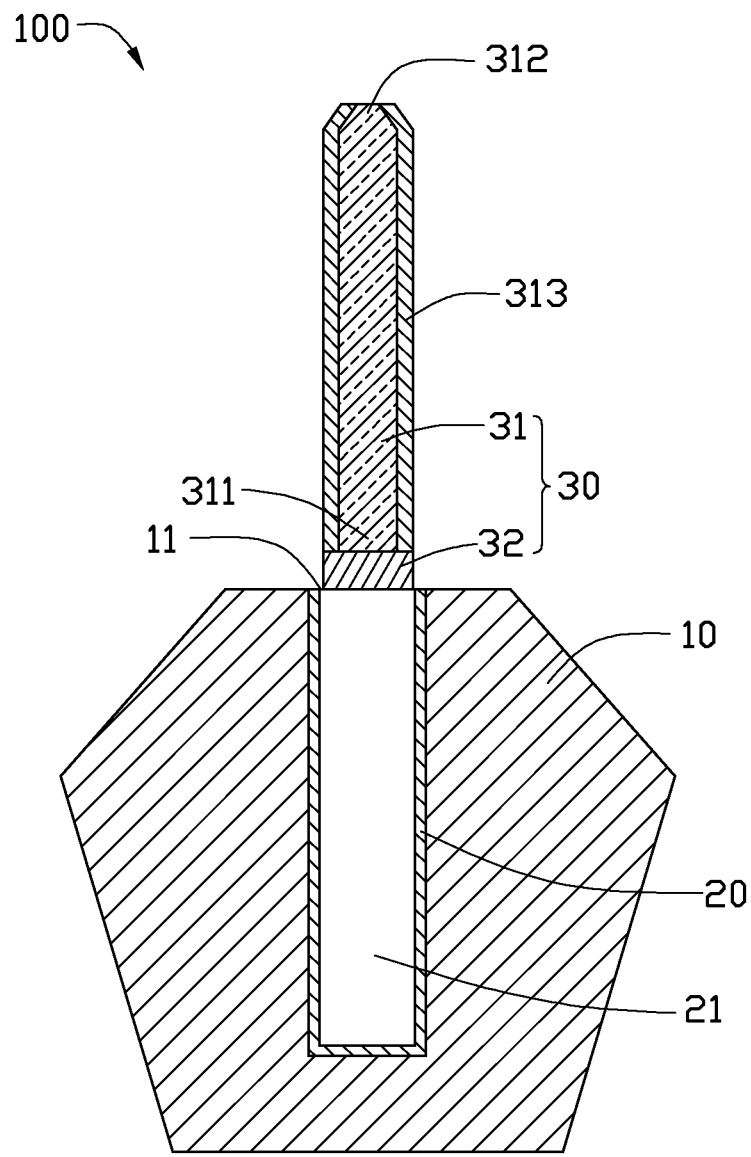
FIG. 1 is a schematic, cross-sectional view of an electric censer, in accordance with a first embodiment of the present disclosure.

Referring to FIG. 1, an electric censer 100 according to a first exemplary embodiment of the present disclosure is shown. The electric censer 100 includes a censer body 10, a receiving unit 20 and an incense branch 30.

The censer body 10 is a hollow container with an opening 11 defined at a top thereof. The censer body 10 is used for receiving a circuit board (not shown) and the incense branch 30. The circuit board is configured to provide electricity for the incense branch 30. The censer body 10 can have various shapes. A removable lid (not shown) can be provided for sealing the opening 11 of the censer body 10 when the incense branch 30 is received in the censer body 10 to prevent dust from entering the censer body 10.

The receiving unit 20 is received in the censer body 10, and includes a hollow tube 21 communicating with the opening 11 of the censer body 10. A shape of the hollow tube 21 is matched with that of the incense branch 30. In the present embodiment, the hollow tube 21 is arranged in a center portion of the censer body 10 and arranged in line with the incense branch 30. The incense branch 30 is arranged on the censer body 10, and can be received in the hollow tube 21 of the receiving unit 20.

The incense branch 30 includes a light guiding bar 31 and a light emitting unit 32 arranged on a first end 311 of the incense branch 30. A second end 312 of the incense branch 30 opposite to the first end 311 acts as a light outputting side. The incense branch 30 extends outwardly from the opening 11 of the censer body 10 when in use, and is received in the hollow tube 21 when not in use. The removable lid covers the opening 11 when the incense branch 30 is received in the hollow tube 21. In the present embodiment, the light guiding bar 31 has a cylindrical shape, and a diameter of the light guiding bar 31 is equal to or slightly less than that of the hollow tube 21. A length of the hollow tube 21 is equal to or larger than that of the light guiding bar 31. The second end 312 of the light guiding bar 31 has a symmetrical coniform shape with a flat top face through which light evenly outputs from the second end 312. The light guiding bar 31 is made of plastic with high pliability. The light emitting unit 32 is arranged on the opening 11 of the hollow tube 21. In the present embodiment, the light emitting unit 32 is an LED, which connects the first end 311 of the light guiding bar 31 by transparent glue. Light emitted from the light emitting unit 32 transmits to the light guiding bar 31, and then travels through the second end 312 to an outside for lightening. In the present embodiment, a reflective layer 313 is arranged on an outer side surface of the light guiding bar 31, to reflect light emitted from the light emitting unit 32 to the second end 312; therefore, no light will leak from the incense branch 30, except the top face of the second end 312, whereby a visual effect of an incense can be obtained and a highly efficient utilization of the light generated by the light emitting unit 32 can be realized.

When the electric censer 100 is not in use, the incense branch 30 is received in the hollow tube 21 for saving the space, and avoiding the incense branch 30 to be broken, and also for convenient transportation.

It can be understood that a dimension of the light emitting unit 32 can be slightly larger than a diameter of the hollow tube 21; therefore, the light emitting unit 32 can be fixed on a predetermined position by the frictional force between the light emitting unit 32 and the hollow tube 21 when the light emitting unit 32 received in the hollow tube 21.

Figure 2:
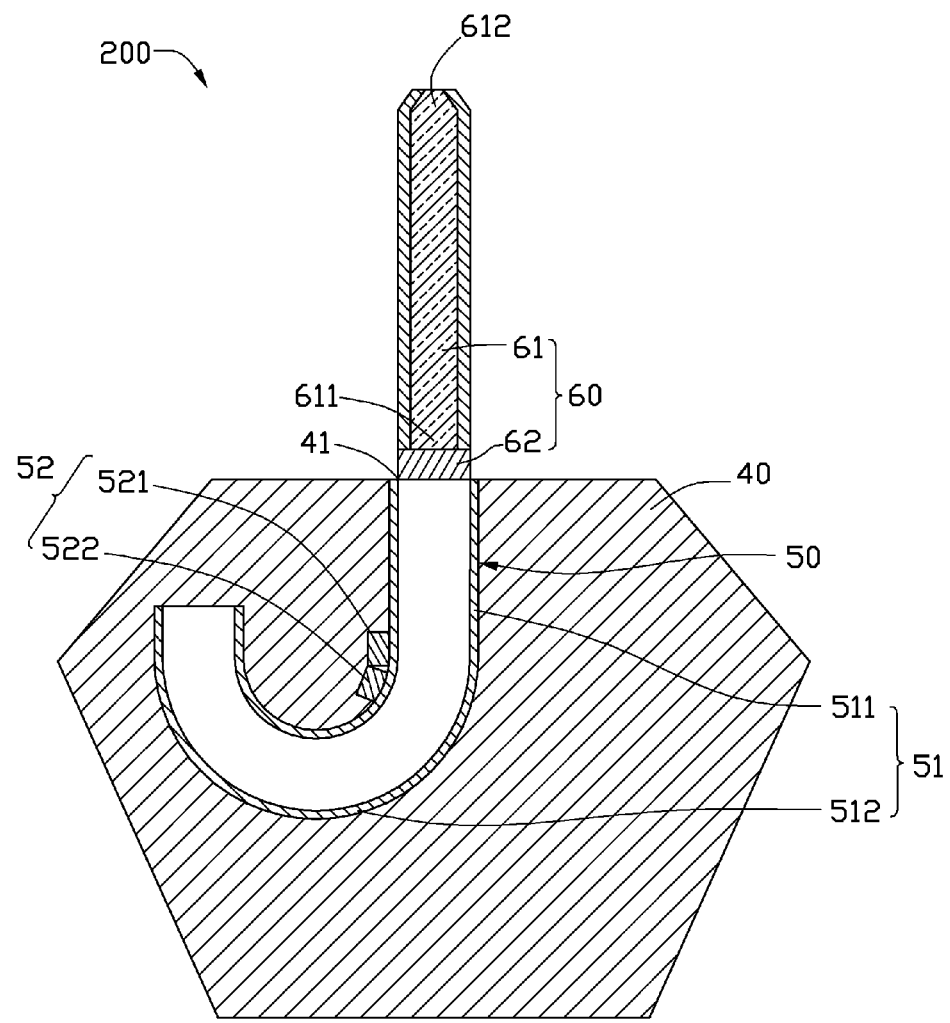
FIG. 2 is a schematic, cross-sectional view of an electric censer, in accordance with a second embodiment of the present disclosure.

Referring to FIG. 2, an electric censer 200 according to a second exemplary embodiment of the present disclosure is shown. The electric censer 200 includes a censer body 40, a receiving unit 50 and an incense branch 60. The censer body 40 and the incense branch 60 are similar to the censer body 10 and the incense branch 30 of the electric censer 100 of the first embodiment, respectively. Differing from the electric censer 100, the receiving unit 50 includes a hollow tuber 51 communicating with the opening 41 of the censer body 40, and a temperature modulator 52 thermally connected to the hollow tube 51.

The incense branch 60 includes a light guiding bar 61 and a light emitting unit 62 arranged on a first end 611 of the incense branch 60. The light guiding bar 61 is made of plastic with high pliability. The intenerate temperature (softening temperature) of the plastic is ranged from 60 to 80 degrees Celsius, and the melting temperature of the plastic is equal to or larger than 100 degrees Celsius.

The hollow tube 51 includes a condensing part 511 communicating with the opening 41 of the censer body 40 and a heating part 512 connected to the condensing part 511 and extending therefrom outwardly. The condensing part 511 is straight and arranged in line with the incense branch 60. The heating part 512 is curved outwardly from a bottom end of the condensing part 511. In the present embodiment, the temperature modulator 52 is a semiconductor temperature modulator such as a Peltier module which has a hot side and a cold side, and includes a cooler 521 thermally connected to the condensing part 511 and a heater 522 thermally connected to the heating part 512. The cooler 521 lowers the temperature of the condensing part 511; therefore, the temperature of the condensing part 511 can decrease below the room temperature. The heater 522 heats the heating part 512; therefore, the temperature of the heating part 512 can reach a range from 60 to 80 degrees Celsius.

Figure 3:
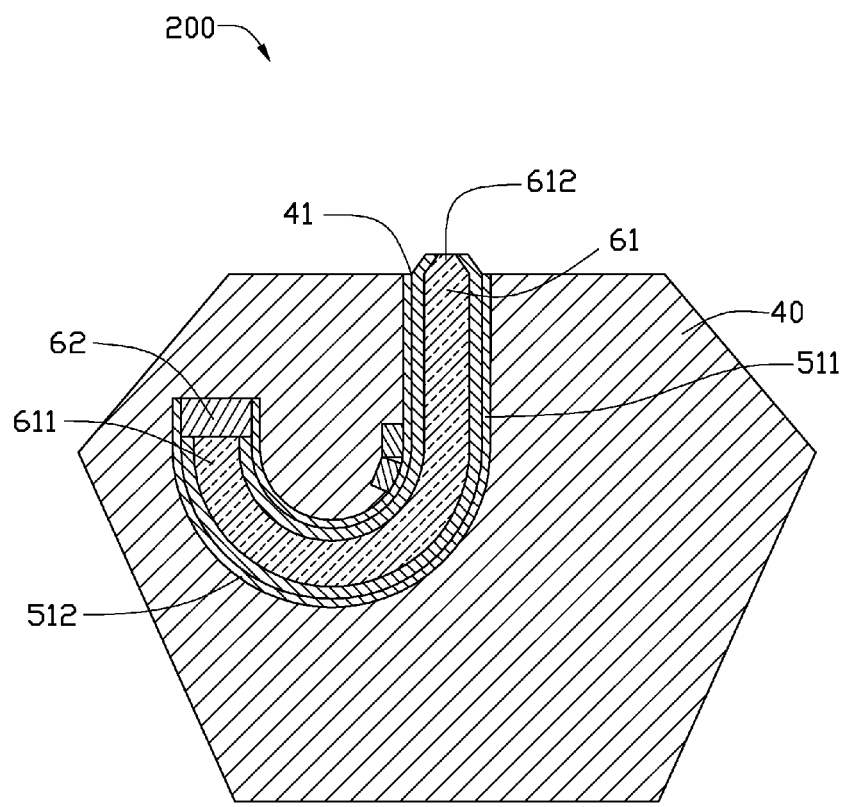
FIG. 3 is a schematic, cross-sectional view of the electric censer of FIG. 2 in another operational state.

Referring to FIG. 3 also, when the electric censer 200 is not in use, the incense branch 60 is depressed into the receiving unit 50, wherein the light emitting unit 62 and the first end 611 of the light guiding bar 61 pass through the condensing part 511 of the hollow tube 51 via the opening 41 of the censer body 40 and reach to the heating part 512. The light guiding bar 61 is heated and intenerated by the heater 522; therefore, the light guiding bar 61 can be bent and received in the hollow tube 51. In the present embodiment, a length of the incense branch 60 is slightly bigger than that of the hollow tube 51, and the second end 612 of the incense branch 60 is always exposed out from the opening 411; therefore, it is convenient for pulling the incense branch 60 out from the hollow tube 51.

When it is necessary to use the electric censer 200, the second end 612 of the light guiding bar 61 is pulled upwardly, during which the first end 611 of the light guiding bar 61 is cooled by the cooler 521 when the first end 611 moves through the condensing part 511; therefore, when the light guiding bar 61 is pulled out from the opening 41, the light guiding bar 61 is in the straight shape of FIG. 2.

In the present embodiment, the electric censer 200 can further include a controller (not shown) for controlling the operation of the temperature modulator 52, thereby to reduce energy consumed.

It is to be further understood that even though numerous characteristics and advantages have been set forth in the foregoing description of embodiments, together with details of the structures and functions of the embodiments, the disclosure is illustrative only; and that changes may be made in detail, especially in matters of shape, size, and arrangement of parts within the principles of the disclosure to the full extent indicated by the broad general meaning of the terms in which the appended claims are expressed.

What is claimed is:

1. An electric censer comprising:
    a censer body, which is a hollow container with an opening defined at a top thereof;
    a receiving unit in the censer body and comprising a hollow tube communicating with the opening of the censer body; and
    an incense branch comprising a light guiding bar and a light emitting unit positioned on a bottom end of the light guiding bar, a top end of the light guiding bar functioning as a light outputting side of the incense branch;
    wherein a position of the light emitting unit is adjustable to be received in an end of the hollow tube remote from the opening by pressing the light guiding bar into the hollow tube or be located adjacent to the opening by pulling the light guiding bar out of the hollow tube; and
    wherein the receiving unit comprises a thermal modulator thermally connected to the hollow tube, the hollow tube comprising a condensing part communicating with the opening of the censer body and a heating part connected to the condensing part extending outwardly from a bottom end of the condensing part, the thermal modulator comprising a cooler in thermal connection with the condensing part and a heater in thermal connection with the heating part.

2. The electric censer according to claim 1, wherein the hollow tube is arranged in line with the incense branch, when the incense branch is pulled out of the hollow tube.

3. The electric censer according to claim 1, wherein the condensing part is arranged in line with the incense branch, when the incense branch is pulled out of the hollow tube.

4. The electric censer according to claim 1, wherein the heating part is curved outwardly from the bottom end of the condensing part.

5. The electric censer according to claim 1, wherein the light guiding bar is made of plastic.

6. The electric censer according to claim 5, wherein an intenerate temperature of the plastic is ranged from 60 to 80 degrees Celsius.

7. The electric censer according to claim 5, wherein a melting temperature of the plastic is no less than 100 degrees Celsius.

8. The electric censer according to claim 1, wherein the light emitting unit comprises an LED and is connected to the bottom end of the light guiding bar by transparent glue.

9. The electric censer according to claim 1, wherein a reflective layer is arranged on an outer side surface of the light guiding bar.

10. An electric censer comprising:
    a censer body, which is a hollow container with an opening defined at a top thereof;
    a receiving unit in the censer body and comprising a hollow tube and a temperature modulator in thermal connection with the hollow tube, the hollow tube comprising a condensing part communicating with the opening of the censer body and a heating part connected to the condensing part; and
    an incense branch comprising a light guiding bar and a light emitting unit positioned on a first end the light guiding bar, a second end of the light guiding bar extending outwardly from the opening of the censer body and being a light outputting side of the incense branch;
    wherein a position of the light emitting unit is adjustable by pressing the light guiding bar.

11. The electric censer according to claim 10, wherein the condensing part is straight and the heating part is curved, the thermal modulator comprising a cooler thermally connected to the condensing part and a heater thermally connected to the heating part, the light guiding bar being intenerated by the heater when the light guiding bar moves through the heating part, and the light guiding bar being cooled by the cooler when the light guiding bar moves through the condensing part.

12. The electric censer according to claim 10, wherein the light guiding bar is made of plastic.

13. The electric censer according to claim 12, wherein an intenerate temperature of the plastic is ranged from 60 to 80 degrees Celsius.

14. The electric censer according to claim 12, wherein a melting temperature of the plastic is no less than 100 degrees Celsius.

15. The electric censer according to claim 10, wherein the light emitting unit comprises an LED and is connected to the first end of the light guiding bar by transparent glue.

16. The electric censer according to claim 10, wherein a reflective layer is arranged on an outer side surface of the light guiding bar.

* * * * *